United States Patent [19]

Allan et al.

[11] 4,126,445

[45] Nov. 21, 1978

[54] SYNTHETIC POLYMERS FURNISHING CONTROLLED RELEASE OF A BIOLOGICALLY ACTIVE COMPONENT DURING DEGRADATION

[75] Inventors: G. Graham Allan, Sreeman A. N. Neogi, both of Seattle, Wash.

[73] Assignee: University of Washington, Seattle, Wash.

[21] Appl. No.: 684,561

[22] Filed: May 10, 1976

Related U.S. Application Data

[62] Division of Ser. No. 184,259, Sep. 27, 1971, Pat. No. 4,062,855.

[51] Int. Cl.$^2$ ................................................. A01N 9/22
[52] U.S. Cl. ................................... 71/94; 71/DIG. 1; 71/85; 71/88; 71/112; 71/115; 424/78; 424/213
[58] Field of Search ................... 424/32, 78, 19; 71/94

[56] References Cited

U.S. PATENT DOCUMENTS

| | | | |
|---|---|---|---|
| 2,621,168 | 12/1952 | Ross et al. | 260/75 N |
| 2,805,213 | 9/1957 | Caldwell et al. | 260/75 S |
| 3,567,119 | 3/1971 | Wilbert | 424/32 |
| 3,852,416 | 12/1974 | Grubb et al. | 424/78 |

FOREIGN PATENT DOCUMENTS 1,212,842  11/1970  United Kingdom.

*Primary Examiner*—V. D. Turner
*Attorney, Agent, or Firm*—Seed, Berry, Vernon & Baynham

[57] ABSTRACT

Synthetic, substantially water-insoluble organic polymers having a backbone or main chain including repeating units of at least one polymer forming biologically active component such as a pesticide are capable of slowly degrading in the medium where their activity is desired to slowly release the free biologically active component and thereby prolong the period of effectiveness of the biologically active component.

5 Claims, No Drawings

SYNTHETIC POLYMERS FURNISHING CONTROLLED RELEASE OF A BIOLOGICALLY ACTIVE COMPONENT DURING DEGRADATION

This is a divisional of application Ser. No. 184,259, filed Sept. 27, 1971, now U.S. Pat. No. 4,062,855.

BACKGROUND OF THE INVENTION

1. Field of the Invention

This invention relates to novel synthetic polymers furnishing a controlled release of biologically active component during degradation and to methods of preparing such.

2. Prior Art Relating to the Disclosure

Pesticides having a very long life, such as DDT and other chlorinated hydrocarbons, have been increasingly under attack due to their residues entering the food chain. Pesticides having relatively short lives have been developed; however, the effective life of these pesticides is shortened by washing away, rain, removal by evaporation, degradation into inactive products, or leaching into the subsoil. If the latter occurs, breakdown of the pesticide into nontoxic residues is not as rapid as at the soil-air interface, thus allowing the pesticides to contaminate underground water sources or streams and lakes with subsequent damage to aquatic and wild life.

Work has been done to increase the effective protection period of such pesticides and to diminish the residual waste of costly chemicals which are the causes of serious pollution problems and damage to wild life by designing systems to release the biologically active component at a controlled rate effective to control the pest but minimize the amount leached out by rain, removed by evaporation, or otherwise.

U.S. Pat. Nos. 2,460,376; 3,127,235; and 3,194,730 teach the concept of adsorbing pesticides on strong absorbents such as silica gel, mica and activated charcoal. These formulations have met with only partial success due to the presence of a highly reversible release mechanism.

The use of polymers to control the release of biologically active compounds is known. U.S. Pat. No. 3,074,845 discloses a physical release mechanism in which an inert absorbent is impregnated with a pesticide and then coated with a urea-formaldehyde resin. U.S. Pat. No. 3,223,513 discloses a mixture of an insecticide with a polymer to obtain an extended life product. U.S. Pat. No. 3,212,967 employs a butyl polyacrylate latex with added O,O-dimethyl-O-(2,4,5-trichlorophenyl)-phosphorothioate. Chlorinated phenols have been incorporated into alkyd resins as esters of tri- or tetra-carboxylic esters of benzene as disclosed in U.S. Pat. No. 3,179,608. U.S. Pat. No. 3,343,941 discloses chemically bonding an herbicide to an alkyd resin by incorporating the herbicide into a reaction mixture of phthalic anhydride or humic acid and glycerol. British patent specification No. 1,212,842 discloses bonding a pesticide directly or through a divalent radical to a polymeric substrate such as forest waste, the chemical bonds between the pesticide and the polymer substrate or divalent radical being hydrolyzable to release the pesticide on a continuous basis.

SUMMARY OF THE INVENTION

This invention is directed to synthetic organic polymers having a backbone or main chain which includes repeating units of at least one polymer-forming biologically active component such as a pesticide. At least a portion of the chemical linkages or groups of the backbone of the polymer are hydrophilic so that when the polymer is put into the medium where its long term activity is desired, such as in the soil, degradation of the backbone of the polymer chain takes place releasing by depolymerization the free biologically active component. In contrast to the controlled release compositions disclosed in British patent specification No. 1,212,842 wherein the pesticide component is chemically grafted as a pendant group onto a polymeric substrate, the polymers of this invention have a main chain or backbone including repeating units of the pesticide moiety. Chemical grafting of a pesticide (P) to a polymer by a hydrolyzable group as described in British patent specification No. 1,212,842 may be illustrated as follows:

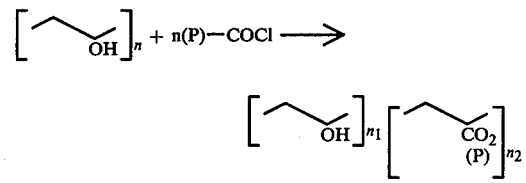

where $n$ is the degree of polymerization and P is the pesticide moiety.

When the polymer is put to use, the pesticide (P) will be freed by hydrolysis of the $-CO_2(P)$ group as illustrated.

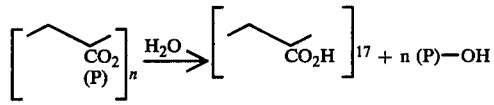

Homopolymerization of a pesticide (P) having more than one reactive group or copolymerization of a pesticide (P) having more than one reactive group with another difunctional compound may be illustrated as follows using, for example, $H_2N-(P)-CO_2H$ as the pesticide;

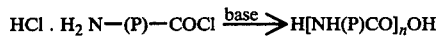

The objects of this invention include providing controlled release polymers which: (1) require much less pesticide for the same period of activity; (2) are easier to handle and are less toxic in polymer form; (3) provide lower risk of damage to plants because of over-application causing phytotoxicity due to the controlled release characteristics of the polymer; (4) are of reduced toxicity to other organisms such as wild life; (5) provide localized release of the pesticide in free form because of application in polymer form; (6) reduce costs due to less frequent application; and (7) minimize pollution hazard.

DETAILED DESCRIPTION OF THE INVENTION

As used in the specification the term "biologically active component" is intended to mean those compounds used to inhibit, repel, exterminate or alter the activities of insects, molds, fungi, bacteria, protozoa, viruses, plants, invertebrates, worms and the like. Generally, the biologically active component is a pesticide selected for a typical end use such as an herbicide, insecticide, miticide, rodenticide, fungicide or the like. The pesticide or biologically active component should be one that is polymer forming; that is, it must have at least two reactive functional groups, each of which possesses a replaceable hydrogen atom or its equivalent. The pesticide may be one which is either self-polymerizable or copolymerizable with a difunctional compound which may or may not have biological activity. If the pesticide moiety is written as (P) and is self-polymerizable, it can be illustrated as follows:

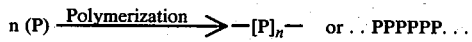

where $n$ is the degree of polymerization. If the pesticide moiety (P) is copolymerizable with a difunctional compound (A), it can be illustrated as follows:

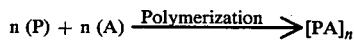

where $n$ is again the degree of polymerization. When either the self-polymerizable or copolymerizable polymers are placed in the medium where their long term activity is desired, such as in the soil, degradation of the polymer chain takes place by random scission to release the free pesticide into the soil. This may be illustrated as follows:

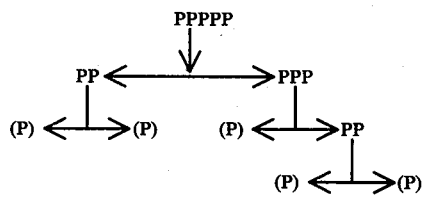

Pesticides which may be polymerized according to this invention include those which have reactive hydrogen atoms capable of forming a series of repeating hydrolyzable bonds which are cleaved by hydrolysis in the medium where pesticide activity is desired. The pesticide should thus be one carrying difunctional groupings such as, for example, —$NH_2$, —COOH, or —OH. Typical of the self-polymerizing and/or copolymerizing pesticides which may be used include those commercially available, such as 3-amino-2,5-dichlorobenzoic acid ("Amiben"), 7-oxabicyclo[2,2,1-heptane]2,3-dicarboxylic acid ("Endothall"), tetrachloroterephthalic acid ("Dacthall"), O,O-dimethylphosphorodithioate, diethyl mercaptosuccinate ("Malathion") and O,O-dimethyl-S-[4,6-diamino-1,3,5-triazine-2-yl methyl]phosphorodithioate ("Menazon").

The rate of release of the pesticide from the polymer is dependent, for a particular set of environmental conditions on: (1) the stability of the P—P bond or —P—A—P bond; (2) the hydrophilicity of the polymer; (3) the kind and number of hydrophilic linkages in the backbone of the polymer; and (4) the degree of polymerization. As regards the degree of polymerization, for example, the probability that a biologically active monomer would be split off by random scission from a polymer having a degree of polymerization "$n$" is approximately $1/n$, suggesting that an increase in the degree of polymerization may affect the release rate and the total effective biologically active protective period of the polymer. The protective period denoted as $t_c$ may be expressed by the formula $$t_c = K_1 - k_2/\sqrt{w}$$

for water soluble polymer backbone and $$t_c = A \cdot \log W + B$$

for water insoluble polymer backbone where $A$, $B$, $K_1$ and $K_2$ are empirical constants and $W$ is the amount of the combinations put in.

The polymers of this invention may be prepared by conventional techniques such as emulsion polymerization, solution polymerization, with or without the use of suitable catalysts. Many of the polymers are formed by condensation/polymerization by dissolving the polymer forming components in a suitable solvent and heating the mixture with stirring to the desired degree of polymerization.

The following examples are exemplary of the invention but are not considered to be limiting.

EXAMPLE I 3,5,6-Trichloro-4-amino picolinic acid (12 g) was refluxed with thionyl chloride for 24 hours. Thionyl chloride was then evaporated off and the residue suspended in chloroform (100 ml) containing triethylamine (15 g) and kept for 3 days. The sticky mass obtained thereafter was churned with water (500 ml) in a Waring blender, filtered and dried to yield a brown powder (8.5 g) of inherent viscosity 0.5 in dimethyl formamide. The average molecular weight of the polymer was 1000. Infrared analysis confirmed the structure. The polymer had a nitrogen content of 12.50 (found) compared to 12.52 (calculated).

EXAMPLE II

Endophthalic acid (60 m mole) was heated with triethylene glycol (62 m mole) and tosylic acid (0.2 g) under nitrogen at 150° C for 6 hours. The polyester produced was a liquid having a molecular weight of about 4000.

EXAMPLE III

The polymerization was carried out by conventional polymerization of ethylene diamine and tetrachloroterephthaloyl chloride. The polymer did not melt up to 300° C. and was insoluble in any common solvent.

EXAMPLE IV

Polymerization was carried out by the same procedure as Example II except polyoxypropyline diamine was used instead of triethylene glycol and no tosylic acid was added. The polymer had a molecular weight of about 4500.

EXAMPLE V

The biological activity of the herbicide polymers of Example I and Example II were evaluated and their release rates followed by bioassay. Controls for the experiments were the monomers corresponding to the polymers used, i.e. endophthalic acid and 4-amino-3,5,6-trichloropicolinic acid. The soil used was a friable, sandy loam with a relatively high organic content. The pH measured on the soil was about 5.8. Forty grams, dry weight, of soil was placed in a series of 500 ml polypropylene cups fitted with drain holes. The soil was fairly homogeneous with any large stones and clumps of organic matter removed. After pressing and moistening the soil, the powdered polymer mixtures of Examples I and II, 250 mg, were mixed with dry soil, 5 g, and placed on the surface of the soil in some of the cups. The same amounts of the controls were used and placed in other cups. A few lettuce seeds were added and pressed into the soil surface of the cup. Every morning 100 ml of water was slowly added to each cup and every week the seeds were replaced by fresh seeds. The plastic cups were supported by wooden frames to allow free drainage. The frame was left in a sheltered position outdoors. Every day observations were made on the germination of the lettuce seeds of the control samples using endophthalic acid and 4-amino-3,5,6-trichloropicolinic acid compared to the polymers of Examples I and II. Table 1 illustrates the period of protection offered by the herbicide monomers compared to the polymeric form in days. As can be seen, the protection offered by the controlled release polymers was considerably greater than the controls.

applying to the medium where the pesticide control is desired a controlled release pesticide polymer for extended release of an effective amount of the active pesticide over an extended period of time, the pesticide polymer made up of at least one polymer-forming pesticide component having at least two reactive functional groups selected from the group consisting of —$NH_2$, —COOH and —OH, the polymer-forming pesticide component polymerized to form a polymer with a polymeric backbone having hydrophilic linkages and a degree of polymerization such that when the pesticide polymer is placed in the medium where its activity is desired the pesticide component is slowly released as a monomer over an extended period of time into the medium by random scission of the hydrophilic linkages in the backbone of the pesticide polymer in an amount effective to control the pest.

2. The method of claim 1 wherein the pesticide component is copolymerized with at least one difunctional monomeric compound.

TABLE 1

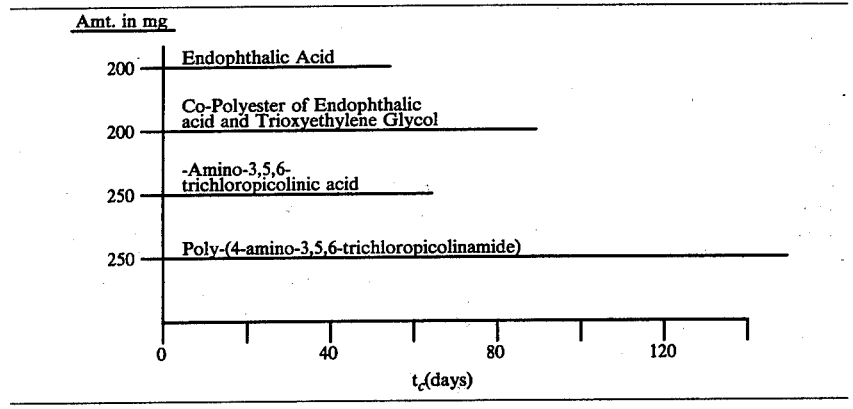

Polymers having molecular weights ranging from about 100 to 5000 have been prepared. The period of effectiveness of the polymers is dependent on the environment where employed, the stability of the chemical bonding between the pesticide components, the degree of polymerization and other factors.

We claim:

1. A method of controlling pests comprising:

3. The method of claim 1 wherein the pesticide component is homo-polymerized.

4. The method of claim 1 wherein the polymer is poly(4-amino-3,5,6-trichloropicolinamide).

5. The method of claim 1 wherein the polymer is a copolymer of endophthalic acid and trioxyethylene glycol.